(12) United States Patent
Tian et al.

(10) Patent No.: US 10,524,665 B2
(45) Date of Patent: Jan. 7, 2020

(54) HANDHELD MOLECULAR IMAGING NAVIGATION SYSTEM

(71) Applicant: INSTITUTE OF AUTOMATION, CHINESE ACADEMY OF SCIENCES, Beijing (CN)

(72) Inventors: Jie Tian, Beijing (CN); Chongwei Chi, Beijing (CN); Xin Yang, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 225 days.

(21) Appl. No.: 15/520,928

(22) PCT Filed: Oct. 22, 2014

(86) PCT No.: PCT/CN2014/089150
§ 371 (c)(1),
(2) Date: Sep. 5, 2017

(87) PCT Pub. No.: WO2016/061754
PCT Pub. Date: Apr. 28, 2016

(65) Prior Publication Data
US 2018/0042481 A1     Feb. 15, 2018

(51) Int. Cl.
*A61B 5/00*        (2006.01)
*H04N 5/225*      (2006.01)
(Continued)

(52) U.S. Cl.
CPC ......... *A61B 5/0071* (2013.01); *H04N 5/2256* (2013.01); *A61B 5/0035* (2013.01);
(Continued)

(58) Field of Classification Search
USPC .................................................... 348/77, 164
See application file for complete search history.

(56) References Cited

U.S. PATENT DOCUMENTS 9,282,259 B2 *  3/2016  Johnson ................... H04N 5/33
9,795,338 B2 * 10/2017  Kang ..................... A61B 5/418
(Continued)

FOREIGN PATENT DOCUMENTS

CN        101125075 A    2/2008
CN        101214142 A    7/2008
(Continued)

OTHER PUBLICATIONS

"International Application No. PCT/CN2014/089150, International Search Report dated Jul. 17, 2015", (Jul. 17, 2015), 6 pgs.
(Continued)

*Primary Examiner* — Nigar Chowdhury
(74) *Attorney, Agent, or Firm* — Schwegman Lundberg & Woessner, P.A.

(57) ABSTRACT

A handheld molecular imaging navigation system comprises a multi-spectral light source module configured to provide light in a plurality of different spectrum bands in a time division control manner according to a control signal sequence to irradiate an inspected object; a time division control module configured to generate the control signal sequence; an optical signal acquisition module configured to acquire a near-infrared fluorescence image and a visible light image of the inspected object in a time division control manner according to the control signal sequence provided by the time division control module; and a processing module configured to perform image processing on the acquired near-infrared fluorescence image and visible light image according to the control signal sequence to fuse the visible light image and the fluorescence image and output the fused image, and output a feedback signal according to the acquired near-infrared fluorescence image and visible light image.

4 Claims, 3 Drawing Sheets

(51) Int. Cl.
*H04N 5/33* (2006.01)
*H04N 5/265* (2006.01)

(52) U.S. Cl.
CPC .......... *A61B 5/0075* (2013.01); *A61B 5/0077* (2013.01); *A61B 5/7235* (2013.01); *A61B 2560/0431* (2013.01); *A61B 2576/00* (2013.01); *H04N 5/265* (2013.01); *H04N 5/332* (2013.01)

(56) References Cited

U.S. PATENT DOCUMENTS

| | | | |
|---|---|---|---|
| 2009/0118578 | A1 | 5/2009 | Takasugi et al. |
| 2010/0238402 | A1* | 9/2010 | Itoh .......................... A61B 3/14 351/206 |
| 2012/0004557 | A1 | 1/2012 | Mcdowall et al. |
| 2012/0044461 | A1* | 2/2012 | Chang ................ G03B 21/2013 353/31 |
| 2012/0169863 | A1* | 7/2012 | Bachelet ............ G01N 15/1463 348/79 |
| 2013/0267857 | A1* | 10/2013 | Takimura ............. A61B 5/0059 600/478 |
| 2014/0028854 | A1* | 1/2014 | Heinke ................... H04N 5/33 348/164 |
| 2014/0042319 | A1* | 2/2014 | Pickett .................... H04N 5/33 250/330 |
| 2014/0099005 | A1* | 4/2014 | Mogi ................. G06K 9/00288 382/118 |
| 2015/0085098 | A1* | 3/2015 | Dowaki .................... G01J 3/44 348/79 |
| 2015/0163418 | A1* | 6/2015 | Chen ..................... H04N 5/332 348/164 |
| 2015/0369730 | A1* | 12/2015 | Schmidt ............. G01N 21/3504 250/208.1 |

FOREIGN PATENT DOCUMENTS

| | | |
|---|---|---|
| CN | 101322644 A | 12/2008 |
| CN | 101498605 A | 8/2009 |
| CN | 102645406 A | 8/2012 |
| CN | 103300812 A | 9/2013 |
| CN | 103385696 A | 11/2013 |
| CN | 104323858 A | 2/2015 |
| CN | 204181710 U | 3/2015 |

OTHER PUBLICATIONS

"International Application No. PCT/CN2014/089150, Written Opinion dated Jul. 17, 2015", (Jul. 17, 2015), 4 pgs.
"Chinese Application Serial No. 201410567427.X, Office Action dated Mar. 14, 2016", w/English Translation, (Mar. 14, 2016), 16 pgs.
"Chinese Application Serial No. 201410567427.X, Office Action dated Aug. 8, 2016", w/English Translation, (Aug. 8, 2016), 7 pgs.

* cited by examiner

HANDHELD MOLECULAR IMAGING NAVIGATION SYSTEM

PRIORITY APPLICATIONS

This application is a U.S. National Stage Filing under 35 U.S.C. 371 from International Application No. PCT/CN2014/089150, filed on 22 Oct. 2014, and published as WO2016/061754 on 28 Apr. 2016; which application and publication are incorporated herein by reference in its entirety.

TECHNICAL FIELD

The present disclosure relates to imaging systems, and more particularly to a handheld molecular imaging navigation system.

BACKGROUND

As a new method and means of the noninvasive visual imaging technology, molecular imaging reflects essentially changes in the physiological and molecular level of organisms and changes in the overall functionality caused by changes in molecular regulation. Therefore, it is an important technique to study life activities of genes, bio-macromolecules and cells in vivo at the molecular level, wherein the basic research of the physiological optical imaging technology in vivo based on molecular technology, tomography, optical imaging technology, and simulation methodology has become one of the hot and difficult spots of research in the molecular imaging field.

Molecular imaging devices combine traditional medical imaging technology with modern molecular biology to observe physiological or pathological changes at cell and molecular levels, and have advantages such as non-invasion, real-time, living body, high specificity, high sensitivity and high resolution imaging etc. The use of the molecular imaging technology, on the one hand, can speed up the research and development of drugs, shorten the time of preclinical study of drugs; and provide more accurate diagnosis, so that a treatment plan best matches a patient's genetic map. On the other hand, the molecular imaging technology can be applied in the field of biomedicine, to achieve purposes such as quantitative analysis, imaging navigation, molecular classification etc. in vivo. However, the system using this method is relatively complex, and the ease of operation and the comfort of use need to be further improved.

Therefore, the present disclosure proposes a handheld molecular imaging navigation system which enhances the application scope by real-time imaging of fluorescence and visible light in different spectrums in a time division control manner.

SUMMARY

The embodiments of the present disclosure provide a handheld molecular imaging navigation system, comprising:

a multi-spectral light source module configured to provide light in a plurality of different spectrum bands in a time division control manner according to a control signal sequence to irradiate an inspected object;

a time division control module configured to generate the control signal sequence;

an optical signal acquisition module configured to acquire a near-infrared fluorescence image and a visible light image of the inspected object in a time division control manner according to the control signal sequence provided by the time division control module; and a processing module configured to perform image processing on the acquired near-infrared fluorescence image and visible light image according to the control signal sequence to fuse the visible light image and the fluorescence image and output the fused image, and output a feedback signal according to the acquired near-infrared fluorescence image and visible light image to optimize the control signal sequence.

Preferably, the handheld molecular imaging system further comprises a handheld system accommodation module configured to accommodate the multi-spectral light source module, the time division control module, and the signal acquisition module.

Preferably, the multi-spectral light source module comprises:

a background light source configured to provide visible light;

a near-infrared light source configured to provide near-infrared light; and a first multi-spectral switcher configured to control the background light source and the near-infrared light source to turn on and turn off alternately according to the time division control signal sequence from the time division control module, to radiate visible light when the optical signal acquisition module acquires the fluorescence image and radiate near-infrared light when the optical signal acquisition module acquires the visible light image.

Preferably, the optical signal acquisition module comprises:

a camera configured to acquire the near-infrared fluorescence image and the visible light image of the inspected object;

a second multi-spectral switcher provided at the front end of the camera;

a timing signal controller configured to receive the control signal sequence from the time division control module and control switch of the second multi-spectral switcher according to the received control signal sequence so that the camera acquires the corresponding visible light image and fluorescence image.

Preferably, the time division control module comprises:

a timing signal generator configured to generate respective control signals according to different light signal sources; and a signal controller configured to convert the control signal from the timing signal generator into a control signal sequence in a system usable format, to control operations of the first multi-spectral switcher and the second multi-spectral switcher.

Preferably, the processing module comprises:

a timing control feedback module configured to monitor the control signal sequence output by the time division control module according to the acquired visible light image and fluorescence image, determine whether it needs to adjust the operations of the first multi-spectral switcher and/or the second multi-spectral switcher, and return a feedback signal to the signal controller based on a determination result; and an image processing module configured to preform image processing on the acquired visible light image and fluorescence image in each timing interval, fuse the processed visible light image and the processed near-infrared fluorescence image and output the fused image.

The embodiments of the present disclosure at least have the following technical effects:

first of all, due to the use of handheld device to acquire images, in the process of biomedical applications, the operation can be simplified, and the application scope can be expanded; and secondly, due to the use of the time division control method, multi-spectral real-time imaging is achieved by image acquisition and image processing. In addition, by setting the multi-spectral switchers and the time division control module, the multi-spectral light source module is switched to cooperate with timing control, which makes it possible to effectively achieve molecular imaging navigation, maximize detected light intensity, and effectively retain useful information. In practical operations, not only strong fluorescence information can be seen, but also visible light information can be seen by an observer, without influences between light in two spectrums.

DETAILED DESCRIPTION

In order to make the purposes, technical solutions and advantages of the present disclosure more apparent and clear, the present disclosure will be further described in detail below in conjunction with specific embodiments and with reference to the accompanying drawings.

The embodiments of the present disclosure provide a handheld molecular imaging navigation system based on excitation fluorescence imaging in molecular imaging.

Figure 1:
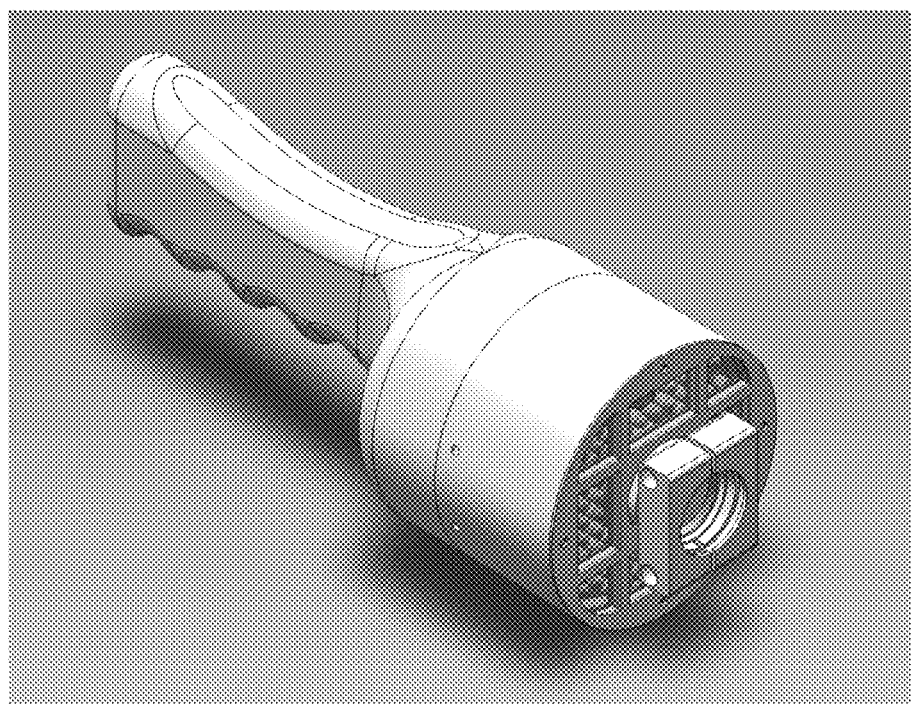
FIG. 1 illustrates a schematic view of an appearance of a handheld system accommodation module according to an embodiment of the present disclosure.
Figure 2:
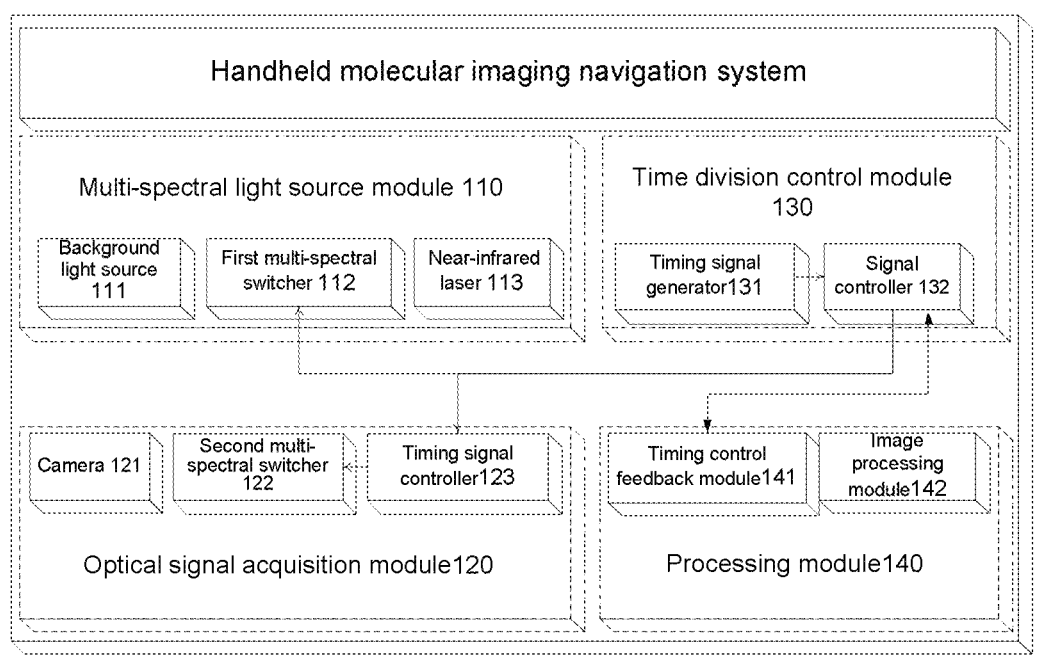
FIG. 2 illustrates a block diagram of a handheld molecular imaging navigation system according to an embodiment of the present disclosure.

FIG. 1 is a schematic view illustrating an appearance of a handheld system accommodation module according to an embodiment of the present disclosure. FIG. 2 is a block diagram illustrating a handheld molecular imaging navigation system according to an embodiment of the present disclosure. As shown in FIG. 2, the handheld molecular imaging navigation system may include a multi-spectral light source module 110 configured to provide light in a plurality of different spectrum bands in a time division control manner to irradiate an inspected object; a time division control module 130 configured to generate a control signal sequence; an optical signal acquisition module 120 configured to acquire a near-infrared fluorescence image and a visible light image of the inspected object in a time division control manner according to the control signal sequence provided by the time division control module; and a processing module 140 configured to perform processing, such as image segmentation, feature extraction, image registration etc., on the acquired near-infrared fluorescence image and visible light image according to the control signal sequence to fuse the visible light image and the fluorescence image and output the fused image, and output a feedback signal according to the acquired near-infrared fluorescence image and visible light image to optimize the control signal sequence. The handheld molecular imaging navigation system further includes the handheld system accommodation module illustrated in FIG. 1 configured to accommodate the multi-spectral light source module, the time division control module, and the signal acquisition module, to facilitate the ease of operation and ensure effective imaging.

Operations of the multi-spectral light source module 110, the optical signal acquisition module 120, the time division control module 130 and the processing module 140 will be described respectively below in detail.

The multi-spectral light source module 110 may include a background light source 111, a first multi-spectral switcher 112 and a near-infrared laser 113. The background light source 111 is used to provide visible light. The near-infrared light source 113 is used to provide near-infrared light and may be provided as a Light Emitting Diode (LED) lamp having a central wavelength of 760 nm. The first multi-spectral switcher 112 controls the background light source 111 and the near-infrared light source 113 to turn on and turn off alternately according to the time division control signal sequence from the time division control module 130, to radiate visible light when the optical signal acquisition module 120 acquires a fluorescence image and radiate near-infrared light when the optical signal acquisition module 120 acquires a visible light background image. A near-infrared light filter having a wavelength of 707 nm to 780 nm may be placed at a front end of the near-infrared light source 113. A visible light filter having a wavelength of 400 nm to 650 nm may be placed at a front end of the background light source 111. Preferably, when a fluorescent sequence signal is radiated, the first multi-spectral switcher 112 is switched to a light filter position 1 where a band pass light filter having a wavelength of 707 nm to 780 nm is placed. When a visible light sequence signal is radiated, the first multi-spectral switcher 112 is switched to a light filter position 2 where no light filter is placed. A wavelength of the visible light radiated by the background light source 111 can be further optimized by placing the band pass light filter having a wavelength of 400 nm to 650 nm at the light filter position 2.

The optical signal acquisition module 120 may include a camera 121, a second multi-spectral switcher 122 and a timing signal controller 123. The camera 121 is used to acquire a near-infrared fluorescence image and a visible light image. Most industrial cameras are suitable for the visible light image. Related parameters of the camera may be set to quantum efficiency higher than 30% at 800 nm, a frame rate greater than 30 fps and an image source size greater than 5 microns. The timing signal controller 123 is used to receive the time division control signal sequence from the time division control module 130 and control the second multi-spectral switcher 122 to switch between a position 1' and a position 2' according to the received time division control signal sequence, so that the camera acquires the corresponding visible light image and fluorescence image. The second multi-spectral switcher 122 is provided at the front end of the camera 121 for switching according to a delayed control signal sequence from the timing signal controller. When the fluorescence image signal arrives, the second multi-spectral switcher 122 is switched to the position 1' where a light filter having a wavelength of 808 nm to 880 nm is placed. When the visible light image signal arrives, the second multi-spectral switcher 122 is switched to the position 2' where no light filter is placed.

The time division control module 130 includes a timing signal generator 131 and a signal controller 132. The timing signal generator 131 generates respective control signals according to different signal sources and transmits the generated control signal to the signal controller 132. The signal controller 132 converts the control signal from the timing signal generator 131 into a control signal sequence in a system usable format and transmits the converted control signal sequence to the first multi-spectral switcher 112 and the timing signal controller 123. The timing signal controller 123 delays the received control signal sequence appropriately and uses the delayed control signal sequence to control an operation of the second multi-spectral switcher 122. Of course, the timing signal controller 123 may be omitted, and the control signal sequence and the delayed control signal sequence are directly generated by the signal controller 132 to control operations of the first multi-spectral switcher 112 and the second multi-spectral switcher 122, respectively.

The processing module 140 includes a timing control feedback module 141 and an image processing module 142. The timing control feedback module 141 monitors the control signal sequence output from the time division control module 130 according to the visible light image and the fluorescence image acquired by the camera 121. Specifically, the timing control feedback module 141 receives the visible light image and the fluorescence image acquired by the camera 121 determines whether it needs to adjust operations of the first multi-spectral switcher 112 and/or the second multi-spectral switcher 112 according to light intensity of the received visible light image and fluorescence image, and returns a feedback signal to the signal controller 132 in a case that it is determined that the operations of the first multi-spectral switcher 112 and/or the second multi-spectral switcher 122 need to be adjusted. The signal controller 132 adjusts the control signal sequence to be transmitted to the respective first multi-spectral switcher 112 and/or second multi-spectral switcher 122 according to the received feedback signal.

For example, if the timing control feedback module 141 determines that brightness of the received visible light image is too large, the timing control feedback module 141 returns a feedback signal to the signal controller 132 to instruct the signal controller 132 to control to shorten time during which the background light source 111 is turned on or increase time during which the near-infrared light source 113 is turned on, or shorten duration during which the visible light image is acquired by the camera 121. When the timing control feedback module 141 determines that the brightness of the received visible light image is too small, the timing control feedback module 141 returns a feedback signal to the signal controller 132 to instruct the signal controller 132 to control to increase the time during which the background light source 111 is turned on or shorten the time during which the near-infrared light source 113 is turned on or extend the duration during which the visible light image is acquired by the camera 121. In addition, the timing control feedback module 141 may also return a feedback signal to the signal controller 132 according to the brightness (i.e., a light intensity parameter) of the received visible light image and fluorescence image, to instruct the signal controller 132 to control to change the corresponding light illumination intensity and/or the corresponding time during which corresponding images are acquired by changing gratings in the first multi-spectral switcher 1 and/or the second multi-spectral switcher 2. It will be appreciated by those skilled in the art that other combinations of the operations of the first multi-spectral switcher 112 and the second multi-spectral switcher 122 may also be employed as long as the operations of the first multi-spectral switcher 112 and/or the second multi-spectral switcher 122 can be adjusted according to the light intensity of the received visible light image and fluorescence image.

In addition, the timing control feedback module 141 may also receive the control signal sequence from the signal controller 132 and a feedback control signal sequence and a second feedback control signal sequence from the first multi-spectral switcher 112 and the second multi-spectral switcher 122 respectively, and compare the control signal sequence with the first feedback control signal sequence and the second feedback control signal sequence respectively. For example, the timing control feedback module 141 may compare respective start and end points of the various control signal sequences. If a timing deviation exceeds a first predetermined threshold but less than a second predetermined threshold, the timing control feedback module 141 feeds information back to the signal controller 132 to adjust the output control signal sequence. If the timing deviation exceeds the second predetermined threshold, the timing control feedback module 141 determines that an error cannot be automatically adjusted, then generates an error report, and transmits the error report to the signal controller 132 to control the component to stop the acquisition, and start operations of the timings after the timings are synchronized.

The image processing module 142 is configured to process the acquired visible light image and fluorescence image in each timing interval. A specific process may include segmentation, feature extraction and pseudo-color transformation of the acquired near-infrared fluorescence image, adjustment and optimization of brightness of the acquired visible light image, fusion of the processed visible light image and the processed near-infrared fluorescence image, and output of the fused image.

Next, a control timing of the molecular imaging navigation system according to the embodiment of the present disclosure will be described in detail with reference to FIGS. 2 and 3.

Figure 3:
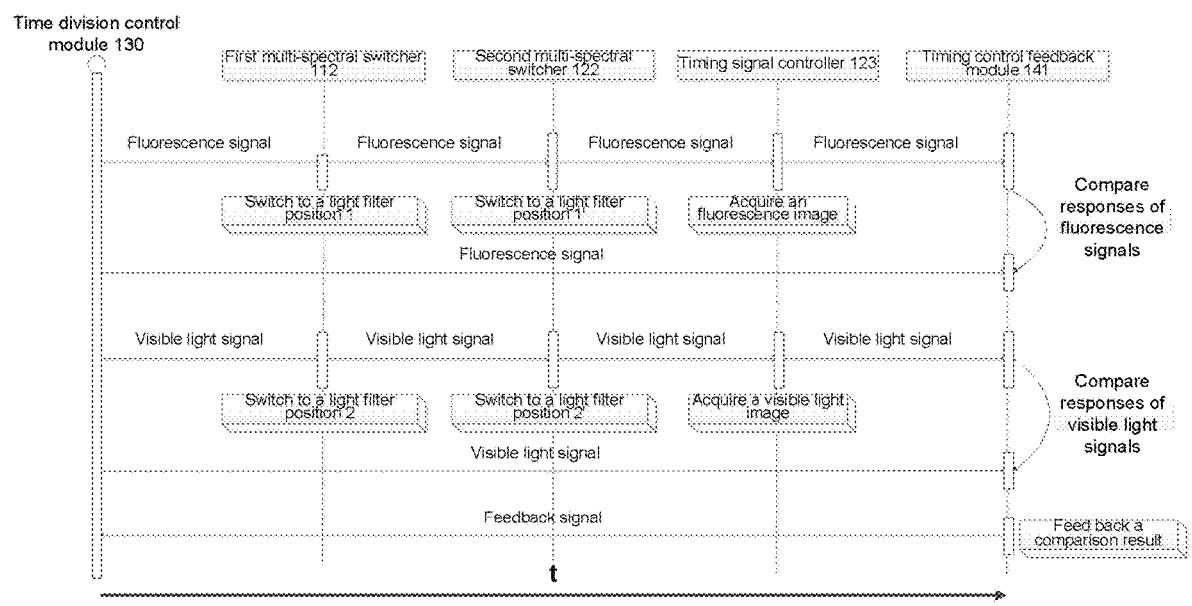
FIG. 3 illustrates a diagram of a control timing of a time division control module in FIG. 2.

FIG. 3 illustrates a diagram of a control timing of the time division control module in FIG. 2. As shown in FIG. 3, the first multi-spectral switcher 112 turns off the background light source 111 and turns on the near-infrared light source 113 at timing t1 according to the control signal sequence from the signal controller 132 to irradiate an inspected object with a fluorescent signal. At this time, the first multi-spectral switcher 112 is switched to a light filter position 1 where a band-pass light filter having a wavelength of 707 nm to 780 nm is placed. The timing signal controller 123 in the optical signal acquisition module 120 receives the control signal sequence from the signal controller 132 and performs corresponding delay on the control signal sequence to control the second multi-spectral switcher 122 to be switched to a position 1' where a light filter having a wavelength of 808 nm to 880 nm is placed when a fluorescence signal reflected from the inspected object arrives, thereby obtaining a fluorescence image of the inspected object and outputting the fluorescence image to the processing module 140.

At timing t2, the background light source 111 is turned on and the near-infrared light source 113 is turned off to irradiate the inspected object with a visible fluorescent signal. At this time, the first multi-spectral switcher 112 is switched to a light filter position 2 where no light filter is placed or a visible light filter having a wavelength of 400 nm to 650 nm is placed. The timing signal controller 123 in the optical signal acquisition module 120 controls the second multi-spectral switcher 122 according to the timing to be switched to a position 2' where no light filter is placed when a visible light signal reflected from the inspected object arrives, thereby obtaining a visible light image of the inspected object and outputting the visible light image to the processing module 140.

A specific process of image processing and excitation fluorescence imaging includes two interrelated processes which are an excitation process and an emission process. In the excitation process, a monochromatic or narrowband excitation light source is used to irradiate a specific imaging region to excite light to enter the interior through a surface and forms a certain light intensity distribution in the interior thereof. In the emission process, the internal fluorophore absorbs energy of external excitation light and converts the energy into emission light having a longer wavelength and lower energy, which is transmitted to the outside and may be detected by a combination of a light filter having a specific wavelength and a detector having high sensitivity. The two processes, i.e., the excitation process and the emission process, may be described by the coupling of two diffusion equations as follows:

$$-\nabla \cdot (Dx(r)\nabla \Phi x(r)) + \mu ax(r)\Phi x(r) = \ominus \delta(r-rl) \quad (3)$$

$$-\nabla \cdot (Dm(r)\nabla \Phi m(r)) + \mu am(r)\Phi m(r) = \Phi x(r)\eta \mu af(r) \quad (4)$$

where $\Omega$ represents a three-dimensional space of an object to be imaged, subscripts x and m represent excitation light and emission light respectively; $\Phi x$ and $\Phi$ represent photon densities; $\mu ax$ and $\mu am$ represent optical absorption coefficients, $\mu sx$ and $\mu sm$ represent optical scattering coefficients, $Dx,m=(3\ \mu ax,am+3\ \mu sx, sm(1-g))-1$ represents a diffusion coefficient, and g represents an anisotropy coefficient.

A Robin boundary condition is added when an excitation fluorescence tomography problem is modeled using the diffusion equations:

$$2D_{x,m}(r)\frac{\partial \Phi_{x,m}(r)}{\partial \vec{n}(r)} + \upsilon \Phi_{x,m}(r) = 0 \quad (5)$$

where $\partial$ represents a surface boundary of the object to be imaged, represents a unit normal vector pointing outward on the surface boundary, and v represents a deviation between optical refraction coefficients inside and outside the boundary. $v=(1-R)/(1+R)$, where the parameter R is given by the following formula:

$$R \approx -1.4399n-2+0.7099n-1+0.6681+0.0636n \quad (6)$$

where n represents a refractive index of a biological tissue, and n≈1.4 for a contactless excitation fluorescence tomography system (with the object to be imaged being in the air).

After finite element discretization is performed on the equations (3) and (4), the following equations in a matrix form may be obtained:

$$K_x\Phi_x=Q_x \quad (7)$$

$$K_m\Phi_m=FX \quad (8)$$

As a light intensity distribution of the external excitation light in the excitation process may be obtained directly by solving the equation (7), the equation may be simplified as:

$$\Phi_m^{means}=K_m^{-1}FX=A^{means}X \quad (9)$$

A least square solution of the equation (9) is obtained by solving the equation (9):

$$\min_X E(X) = \|AX - \Phi\|_2^2 \quad (10)$$

With the above calculations, the light intensity distribution is obtained until a number of support set elements exceeds a certain threshold or a residual thereof is less than a threshold.

The purposes, technical solutions and advantages of the disclosure have been further described in detail in the foregoing detailed description, and it is to be understood that the foregoing is merely specific embodiments of the present disclosure and is not intended to limit the present disclosure, Any modification, equivalent substitution, improvement etc. which is made within the spirit and principles of the present disclosure is intended to be included within the protection scope of the present disclosure.

We claim:

1. A handheld molecular imaging navigation system, comprising:

a multi-spectral light source module configured to provide light in a plurality of different spectrum bands in a time division control manner according to a control signal sequence to irradiate an inspected object;

a time division control module configured to generate the control signal sequence;

an optical signal acquisition module configured to acquire a near-infrared fluorescence image and a visible light image of the inspected object in a time division control manner according to the control signal sequence provided by the time division control module; and a processing module configured to perform image processing on the acquired near-infrared fluorescence image and visible light image according to the control signal sequence to fuse the visible light image and the fluorescence image and output the fused image, and output a feedback signal according to the acquired near-infrared fluorescence image and visible light image to optimize the control signal sequence;

wherein the optical signal acquisition module comprises:

a camera configured to acquire the near-infrared fluorescence image and the visible light image of the inspected object;

a second multi-spectral switcher provided at the front end of the camera; and a timing signal controller configured to receive the control signal sequence from the time division control module and control switch of the second multi-spectral switcher according to the received control signal sequence so that the camera acquires the corresponding visible light image and fluorescence image;

and wherein the processing module comprises:

a timing control feedback module configured to monitor the control signal sequence output by the time division control module according to the acquired visible light image and fluorescence image, determine whether it needs to adjust the operations of the first multi-spectral switcher and/or the second multi-spectral switcher, and return a feedback signal to the signal controller based on a determination result; and an image processing module configured to preform image processing on the acquired visible light image and fluorescence image in each timing interval, fuse the processed visible light image and the processed near-infrared fluorescence image and output the fused image.

2. The handheld molecular imaging system according to claim 1, further comprising a handheld system accommodation module configured to accommodate the multi-spectral light source module, the time division control module, and the signal acquisition module.

3. The handheld molecular imaging system according to claim 1, wherein the multi-spectral light source module comprises:
- a background light source configured to provide visible light;
- a near-infrared light source configured to provide near-infrared light; and
- a first multi-spectral switcher configured to control the background light source and the near-infrared light source to turn on and turn off alternately according to the time division control signal sequence from the time division control module, to radiate visible light when the optical signal acquisition module acquires the fluorescence image and radiate near-infrared light when the optical signal acquisition module acquires the visible light image.

4. The handheld molecular imaging system according to claim 1, wherein the time division control module comprises:
- a timing signal generator configured to generate respective control signals according to different signal sources; and
- a signal controller configured to convert the control signal from the timing signal generator into a control signal sequence in a system usable format, to control operations of the first multi-spectral switcher and the second multi-spectral switcher.

* * * * *